United States Patent [19]

Nencioni et al.

[11] Patent Number: 5,206,014
[45] Date of Patent: Apr. 27, 1993

[54] SYNTHETIC NONAPEPTIDE FOR USE AS AN ADJUVANT

[75] Inventors: Luciano Nencioni; Guido Antoni; Diana Boraschi; Aldo Tagliabue, all of Siena, Italy

[73] Assignee: Sclavo, S.p.A., Siena, Italy

[21] Appl. No.: 156,301

[22] Filed: Feb. 12, 1988

[30] Foreign Application Priority Data

Feb. 20, 1987 [IT] Italy .................. 19434 A/87

[51] Int. Cl.$^5$ ................................ C07K 7/06
[52] U.S. Cl. .................... 424/88; 514/15; 530/328
[58] Field of Search .............. 530/328; 514/15; 424/88

[56] References Cited

U.S. PATENT DOCUMENTS 4,283,328  8/1981  Stammer ............... 530/328
4,774,320  9/1988  Tagliabue et al. ........ 530/328
4,845,079  7/1989  Luly et al. ............. 514/18

OTHER PUBLICATIONS

March et al. *Nature* (1985) 315:641–647.
Auron et al. *Proc. Nat. Acad. Sci.* (1984) 81:7907–7911.
Bensi et al. *Gene.* (1987) 52:95–101.
Clark et al. *Nucleic Acids Res.* (1986) 14:7897–7914.

*Primary Examiner*—Lester L. Lee
*Attorney, Agent, or Firm*—Hedman, Gibson & Costigan

[57] ABSTRACT

The specification relates to a synthetic peptide converted into a salt comprising one or more amine groups and capable of potentiating in vivo the primary and secondary antibody response to thymo-dependent and thymo-independent antigens having low immunogenicity.

Injectable preparations comprising a solution of the peptide in a pharmacologically acceptable solvent are particularly useful as adjuvants in therapy.

11 Claims, 4 Drawing Sheets

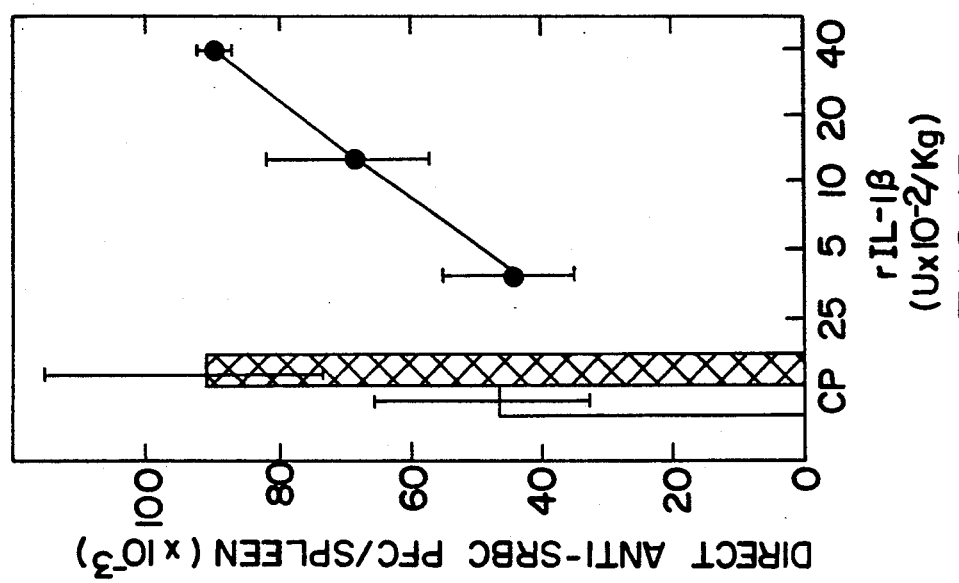
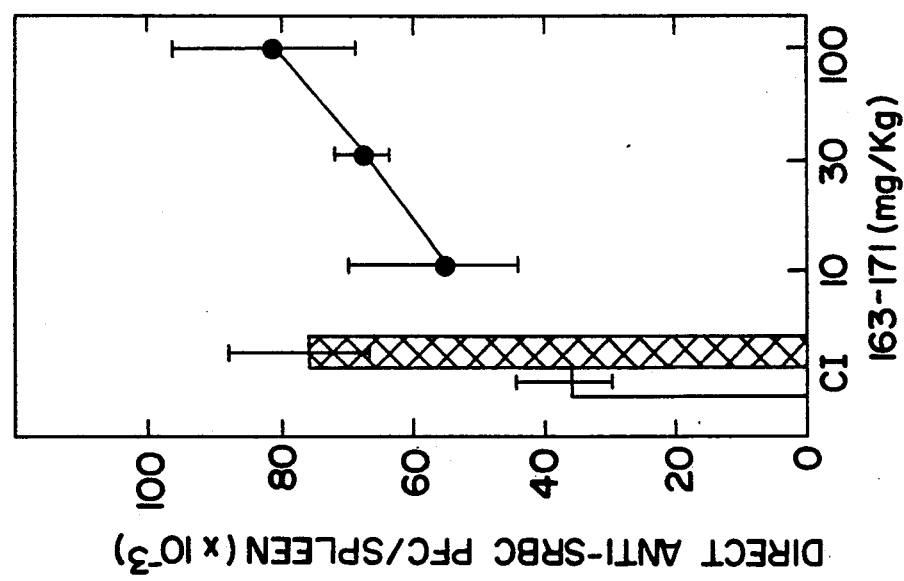

SYNTHETIC NONAPEPTIDE FOR USE AS AN ADJUVANT

The invention relates to a preparation for use as an adjuvant in therapy and comprising a solution of a synthetic peptide converted into a salt comprising one or more amine groups and capable of potentiating in vivo the antibody response to antigens having low immunogenicity. The solution is in a pharmacologically acceptable solvent.

Antigens are defined as any substance which is foreign to a living organism and on coming into contact with the immune system thereof, activates a complex mechanism of cellular interactions which tend to eliminate the antigen and restore the previous equilibrium.

Characteristic features of an antigen are: the capacity to induce production of specific antibodies (immunogenicity) capable of selectively bonding to it (antigenicity) and inactivating it.

The immune response, which is the best defense mechanism of an organism against an infective process, can be deliberately stimulated by administering an antigen via a vaccine.

Some antigens, however, have low immunogenicity and stimulate an antibody response in vivo which is insufficient to give effective immunity to the organism.

As is known in the art, the immunogenicity of an antigen can be improved if it is administered together with adjuvants such as killed bacteria or immunologically inert substances which are capable of increasing the concentration of the antigens presented to the immune system.

One of the most commonly-used substances is Freund adjuvant, an emulsion of mineral oil and water mixed with killed bacteria.

The antigen is introduced into the emulsion and forms a deposit from which it is slowly released and simultaneously the killed bacteria attract cells having a specific immune response function towards the deposit.

This adjuvant, though one of the most potent at present commercially available has disadvantages: for example it causes acute pain and sometimes results in an abscess at the place of injection.

Alum or aluminium hydroxide, used as an alternative to Freund adjuvant, is also unsatisfactory in some respects, particularly in view of its inefficiency towards synthetic antigens and thymo-independent antigens. Numerous adjuvants of bacterial or chemical origin have therefore been proposed in the prior art, but up till now none of them have turned out to be both highly efficient and free from side-effects.

Examples are mycobacteria which act only on the immune response of thymo-dependent antigens (Eisen H. N. 1973 Antibody Formation, in Microbiology, 2nd edition, p. 481, Edit. Harper and Row Hagerstown) and human 1-interleukin (IL-1), a substance produced from cells of the monocyte-macrophage line.

IL-1 does in fact appear to be involved in the defense of the host in response to infections of various origin (Dinarello, C. A. Rev. Infect. Dis. 6, 51, 1984) and production thereof can be stimulated by using inducing agents of bacterial origin (Mizel, S. B. in Microbiology, p. 82, 1980).

When injected into the mouse, interleucine 1 is also capable of increasing the serum level the secondary response to a protein antigen (Staruch M. J. and Wood, J. Immunol. 130, 2191 (1983)).

However, IL-1, besides amplifying the immune response, has other non-immunological activities such as the capacity to induce fever, To induce prostaglandin $E_2$, proteins in the acute phase and to activate neutrophils, which limits its use as an adjuvant in human vaccines.

A need has therefore been felt in the art for adjuvants capable of stimulating the antibody response to both thymo-dependent and thymo-independent antigens having low immunogenicity, without inducing undesirable side-effects.

It has now been found that this requirement can be satisfied by the peptide according to the invention.

One object of the invention, therefore is a preparation for of use as an adjuvant and comprising a sterile solution of a synthetic peptide converted into a salt comprising one or more amine groups and capable of potentiating in vivo the primary and secondary response to thymo-dependent and thymo-independent antigens having low immunogenicity in a pharmacologically acceptable solvent.

Another object of the invention is the use of the preparation in therapy.

Other objects of the invention will be clear from the following specification and examples.

More particularly the peptide according to the invention is a synthetic nonapeptide converted into a salt comprising one or more amino groups and having the following aminoacid sequence corresponding to the fragment 163–171 of human interleukin 1-β:

Val-Gln-Gly-Glu-Glu-Ser-Asn-Asp-Lys-X     (I)

where: Val=L-Valine; Gln=L-Glutamine; Gly=Glycine; Glu=L-Glutamic acid; Ser=L-Serine; Asn=L-Asparagine; Asp=L-Aspartic acid; Lys=L-Lysine and X=OH.

More particularly the peptide according to the invention is the hydrochloride or trifluoroacetate of the nonapeptide having the sequence (I).

These peptides, hereinafter called peptide 163–171.HCl and peptide 163–171.TFA, can be synthesized by one of the generally known techniques.

More particularly, peptide 163–171.TFA is prepared by the method described in the co-pending Italian patent application No. 19338 A/86. According to the invention, the hydrochloride of peptide 163–171 is prepared by dissolving the trifluoroacetate peptide in water and seeding the resulting solution in a column of Amberlite in Cl⁻ form. The column is then eluted with water and the eluate is freeze-dried. This method gives peptide 163–171.HCl with a 90% yield and a content of about 2 mols of chlorine per mol of peptide as measured with an electrode sensitive to Cl⁻ ions.

These peptides in salt form, when assayed in vivo, are capable of potentiating the primary and secondary antibody response to thymo-dependent and thymo-independent antigens having low immunogenicity without inducing the undesirable side-effects characteristic of interleukin 1.

Antigens—substances of protein or polysaccharide nature—are classified as thymo-dependent or thymo-independent depending on whether T helper cells participate in the antibody response.

In this respect, many polysaccharide antigens behave like thymo-independent antigens.

More particularly, the immunostimulating activity of peptides 163–171 TFA and 163–171.HCl were assayed in the antibody response to sheep's red blood compuscles, thymo-dependent antigens and in response to the polysaccharide of Streptococcus pneumoniae serotype 3 (SIII), a thymo-independent antigen having low immunogenicity by using the method of haemolysis of plaques described by Cunningham A. J. and Szenberg (Immunology, 14, 599, 1968).

The method consists in determining the number of cells which secrete antibodies specific to a given antigen. It consists in immunizing mice with the antigen to be assayed, placing lymphocytes obtained from the spleen of the immunized mice in contact with the same antigen, and finally in detecting the haemolysis plaques by adding complement.

Lysis zones (plaque-forming cells PFC) are observed at the place where the antigen-antibody reaction occurs, i.e. at each cell producing specific antibodies. This method, called the direct method, shows the antibody-secreting cells of Class IgM specific to the primary response to the immunization antigen.

The number of IgG class antibody-secreting cells characteristic of the secondary response is determined, before the complement is added, by adding a direct rabbit antiserum against mouse immunoglobulins.

According to the invention, therefore, anti-body secreting cells of Classes IgM and IgG are determined by isolating lymphocytes from the spleen of mice immunized with SRBC and SIII antigens and treated by various methods and with various doses of peptide 163-171.TFA and peptide 163-171.HCl. To this end use has been made with identical results of inbred male C3H/HeNCr1BR mice and male and female C3H/HeJ mice weighing about 25 g. According to the invention, SRBC and SIII antigens previously dissolved in phosphate buffer (PBS) were inoculated in the mice, intravenously and intraperitoneally respectively, at a concentration of $1-2 \times 10^8$ SRBC/0.2 ml of PBS and 0.5 μg/0.5 ml of PBS.

The peptides in salt form were then introduced into the animals in individual doses, either intraperitoneally or intravenously, together with or separately from the antigens in concentrations of 1 pg/kg to 100 mg/kg body weight in the form of sterile solutions in a pharmacologically acceptable solvent.

The solvents may be e.g. water, physiological solution or saline phosphate buffer.

More particularly, saline phosphate was used. The resulting solution, before being inoculated in the mice, was brought to neutral pH with an inorganic base chosen from NaOH and KOH.

The number of antibody-secreting cells of Class IgM, measured as PFC/spleen at various times after immunization showed that the peptides had an efficient immunostimulating activity at all times and there was no variation in the kinetics of the immune response.

It was also observed that the activity depends on the concentration of the peptide administered and that in the case of peptide 163-171 TFA the effect is maximum at a dose of 100 mg/kg when the peptide is intraperitoneally inoculated together with the immunising antigens.

A significant increase in the PFC/spleen was also observed when peptide 163-171 was intraperitoneally administered at the maximum dose of 100 mg/kg two days before and two days after immunization.

Finally, it was observed that the trifluoroacetate peptide, when introduced intraperitoneally for three consecutive days before immunization and at a daily dose 10 to 100 times smaller than the optimum dose, induces an increase in the PFC/spleen equal to that obtained by introducing the optimum dose together with the antigens.

According to the invention, and for the purpose of checking the effect on immunostimulating activity of the method of administration, the two peptides were introduced into mice intravenously together with immunization antigens.

It was thus found that peptides have an activity, in terms of optimum doses necessary to obtain an immunostimulating effect on the primary and secondary response to antigens having low immunogenicity, which is more efficient than the activity obtained by the intraperitoneal method.

It has also been found that the hydrochloride form of peptide 163-171 is, surprisingly, significantly more active than the trifluoroacetate form.

The maximum increase in the primary response to SRBC is obtained at doses of 10 pg-1 ng/kg for peptide 163-171.HCl and 10-100 μg/kg for peptide 163-171.TFA.

Correspondingly, the maximum increase in the secondary response to SRBC is obtained at doses of 10 ng-1 μg/kg of peptide 163-171.HCl and 100 μg/kg of 163-171.TFA.

Finally, significant increases in the primary response to SIII were observed at doses of 1-100 pg/kg of peptide 163-171.HCl.

The optimum intravenous dose of human recombinant IL-1β is 100 pg/kg.

Accordingly, the peptides are suitable as adjuvants in the formulation of vaccines.

Peptide 163-171 in hydrochloride form is particularly suitable for the purposes according to the invention.

Peptides 163-171 according to the invention can be used as such or in the form of preparations as adjuvants for vaccines having low immunogenicity.

A preparation according to the invention can be made by dissolving peptide 163-171 in salt form in a pharmacologically acceptable sterile solvent, preferably chosen from among water or buffer saline solution, in a concentration such as to potentiate the primary and secondary antibody response to thymo-dependent and thymo-independent antigens having low immunogenicity.

Preferably the amounts of peptide used are between 1 pg and 100 mg/kg depending on the method of administration.

According to the invention, the preparation can be administered intravenously or intraperitoneally or intramuscularly together with or separately from the immunization antigens. In another embodiment, the preparation according to the invention can be mixed with suitable quantities of thymo-dependent or thymo-independent, natural or synthetic antigens having low immunogenicity and the resulting compositions can be used as vaccines in human or animal therapy.

BRIEF DESCRIPTION OF THE DRAWINGS

FIG. 1: Immunostimulating effect of peptide 163-171 TFA (P: 12-36-100 mg/kg) (FIG. 1-A) and of human interleucine 1-β (500-1000-2000-4000 U/kg) (FIG. 1-B) on the primary response to SRBC measured as PFC/spleen.

The direct anti-SRBC PFC in the primary response are determined four days after administration of SRBC in a saline phosphate buffer (C), SRBC and human interleucine 1-β (I) and SRBC and peptide 163-171 (P).

The vertical lines represent the 95% confidence limits.

Statistical significance:

Area A: All groups versus control: p≤0.01

Area B: Peptide 163-171 versus control: p≤0.01; human IL-1β 4000

U/kg versus control: non-significant; all other groups versus control: p=0.05.

Figure 2:
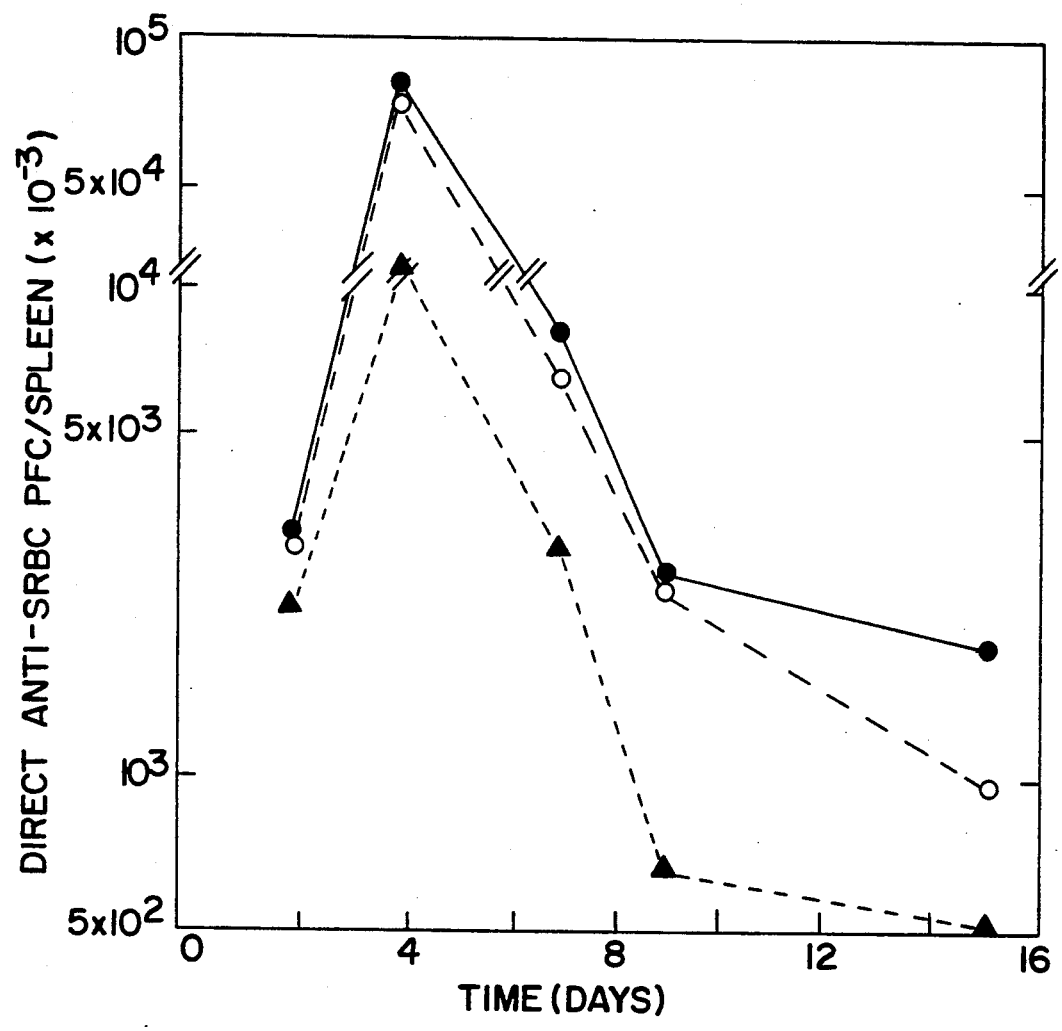

FIG. 2: In vivo kinetics of primary response to SRBC. Evaluation of effects of peptide 163-171 (100 mg/kg; ●...●, Il-1β (2000 U/kg; (0...0) and PBS (▲...▲) on the primary antibody response at various times from inoculation with antigen SRBC.

Statistical significance: peptide versus control: p≤0.05 (days +2 and +4) and p≤0.01 (other days): IL-1β versus control: p≤0.05 (days +4 and +7) and p≤0.01 (other days).

Figure 3:
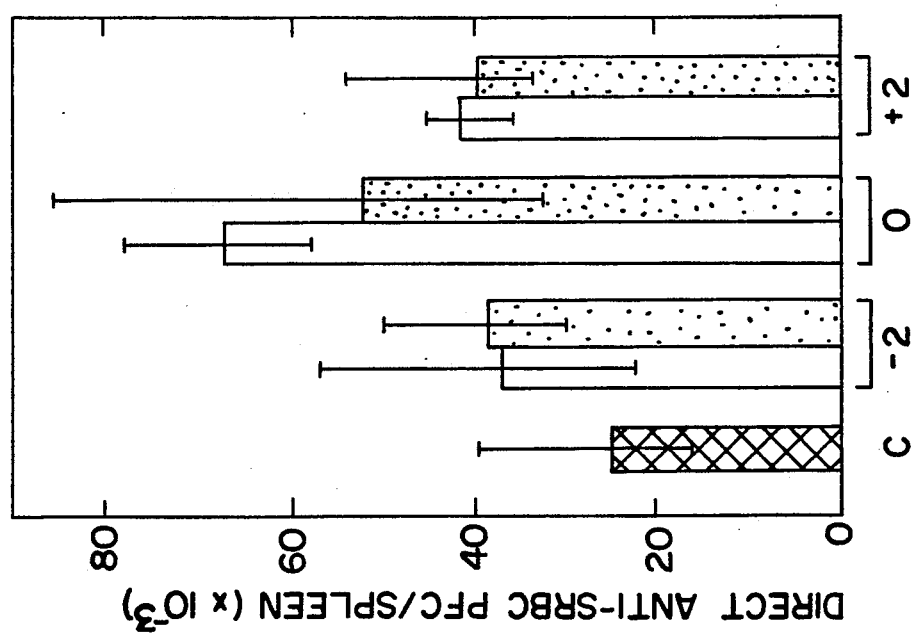

FIG. 3: Kinetics of the effect of peptide 163-171 TFA (100 mg/kg) and IL 1-β(2000 U/kg) on the primary antibody response to SRBC. Peptides 163-171 TFA and IL 1β are inoculated two days before, at the same time and two days after immunisation with SRBC and the PFC/spleen are determined four days after immunisation.

The vertical lines represent the 95% confidence limits. Statistical significance of all groups versus control: p≤0.05.

Figure 4:
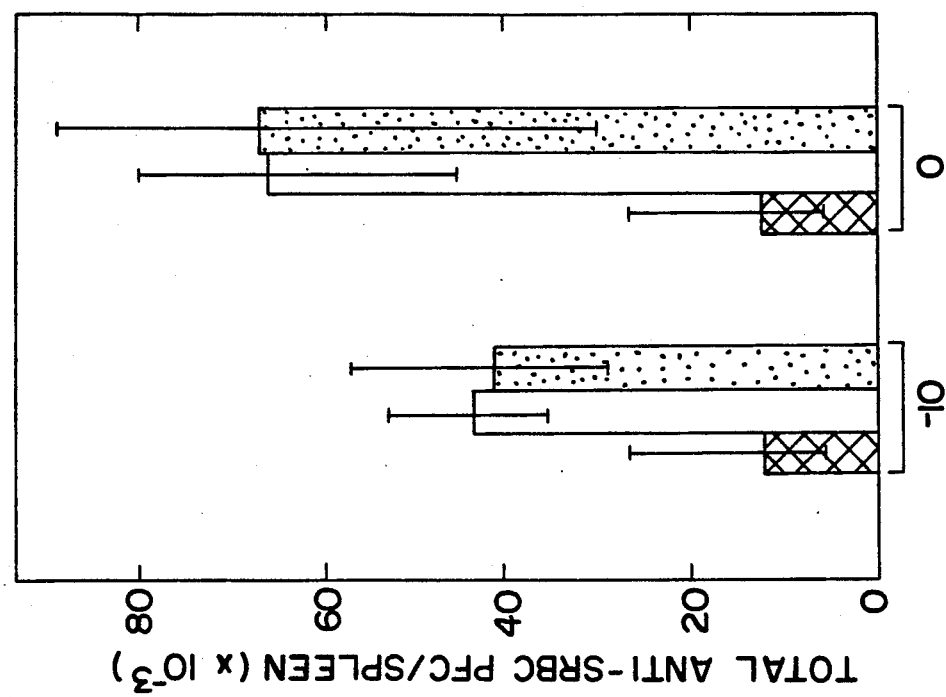

FIG. 4: Comparison of the effect of two different administration times on peptide 163-171 TFA and human interleukin 1-β on the in vivo secondary responde to SRBC.

Peptide 163-171.TFA (100 mg/kg □, IL-1-β (2000 U/kg ▦) and PBS (▓) are administered together with the first (day - 10) and the second (day 0) antigen inoculum.

The vertical lines represent the 95% confidence limits. Statistical significance: all groups versus control: p≤0.01.

Figure 5:
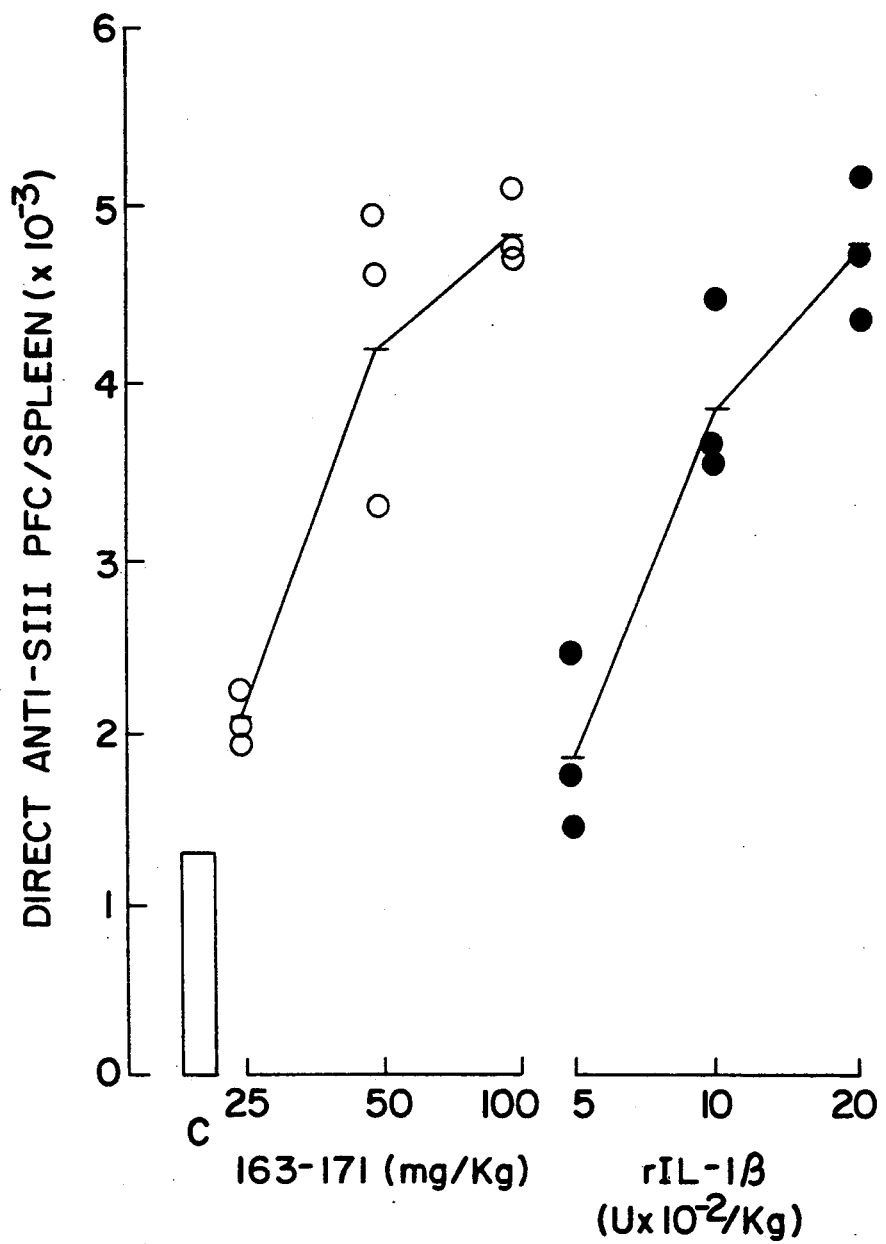

FIG. 5: Effect of peptide 163-171.TFA (0) (12, 36, 100 mg/kg) and human interleukin 1-β (●) (500 - 1000 - 2000 U/kg) on the primary response to SIII compared with PBS (control □. Statistical significance: IL-1-β (500 U/kg) versus control: non-significant; all other groups versus control: p≤0.01.

The following experimental examples non-limitatively illustrate the invention.

EXAMPLE 1

Determination of the immunostimulating effect of peptide 163-171.TFA on the thymo-dependent antigen SRBC 24 C3H/HeNcr1BR inbred male mice (CALCO-ITALIA) aged 10-12 weeks and weighing about 25 g were intravenously treated with 0.2 ml saline phosphate buffer (PBS) containing $1-2 \times 10^8$ sheep's red corpuscles (SCLAVO). After 2 hours the mice were intraperitoneally treated as follows: 3 mice with 0.2 ml PBS, 4 groups of 3 mice with 0.2 ml of PBS containing 500 - 1000 - 2000 and 4000 U/kg of human interleukin 1β (Genzyme Corporation Boston) and 3 groups of 3 mice with 0.2 ml PBS respectively containing 12, 36 and 100 mg/kg of peptide 163-171.

The solutions containing peptide, before being inoculated, were brought to neutral pH with 0.1 N NaOH.

After 4 days the mice were killed and the spleens were removed and mechanically dissociated to separate the lymphocytes.

After being isolated, the lymphocytes were washed three times, each time with 15 ml of minimum culture medium containing Earle salts (M.E.M) (M.A. Bioproducts Walkersville) and then resuspended in 1 ml of the same culture medium at a final concentration of 150,000 cells. 0.1 ml of each cell suspension was successively diluted (1:10 and 1:1000) with MEM culture medium and 100 μl of each dilution were twice added to wells of microplates containing 25 μl of MEM culture medium, 25 μl of a 10% solution of SRBC antigens and 25 μl of guinea-pig complement at a final dilution of 1:64.

The entire suspension was immediately transferred by capillary action from each well to superposed slides.

The slides, sealed at the edges with paraffin, were then incubated in a thermostat at 37° C. for one hour. At the end of this period, the plaques of direct haemolysis were counted using a light-contrast visor, indicating the number of lymphocytes secreting antibodies (PFC). The thus-detected antibodies were in Class IgM, specific to the primary antibody response.

The results in FIGS. 1A and 1B show an increase in the number of plaques/spleen in the presence of peptide 163-171.TFA and human IL-1-β, depending on the dose and at a maximum at a dose of 100 mg/kg peptide.

EXAMPLE 2

Evaluation of the immunostimulating effect of peptide 163-171.TFA at various times after inoculation with SRBC The mice were treated as in Example 1 hereinbefore, by being intraperitoneally inoculated, 2 hours after administration of SRBC, with 100 mg/kg of peptide 163-171 and 2000 U/kg of human IL-1β.

The immunostimulating activity of peptide 163-171 and IL-1β were then determined at 2, 4, 7, 9 and 15 days after inoculation, by isolating the lymphocytes from the spleen of the treated rats and counting the number of PFC/spleen.

The results, given in FIG. 2, show significant immunostimulating activity by peptide 163-171.TFA at all times (maximum after 4 days) and the absence of a variation in the kinetics of the primary antibody response.

EXAMPLE 3

Kinetics of the immunostimulating effect of peptide 163-171.TFA on the primary response to SRBC 3 groups each of 9 mice were treated as follows:

A) The first group, divided into three sub-groups each of three mice, were given 100 mg/kg peptide 163-171.TFA, 2000 U/kg of human IL-1β and 0.2 ml of PBS two days before immunization with SRBC;

B) The second group, divided into three sub-groups each of three mice, were treated with 100 mg/kg of peptide 163-171.TFA. 2000 U/kg of IL-1β and 0.2 ml of PBS, two hours after immunization with SRBC, and finally C) Third group, divided into three sub-groups each of three mice, were treated with 100 mg/kg of peptide 163-171,TFA 2000 U/kg of IL-1β and 0.2 ml of PBS two days after immunization with SRBC.

The results, given in FIG. 3, show a significant increase in the PFC/spleen in the presence of peptide 163-171.TFA as measured four days after immunization, in the case both of the mice treated as in A) and mice treated as in B) and C).

EXAMPLE 4

Determination of the immunostimulating activity of peptide 163-171 on the secondary antibody response to SRBC Mice immunized with SRBC as in Example 1 hereinbefore were intraperitoneally re-inoculated four days after the first inoculation with a similar dose of SRBC antigens and simultaneously with 12, 36, 100 mg/kg peptide 163-171.TFA and 500 - 1000 - 2000 U/kg of human IL-1-$\beta$.

The immunostimulating activity of the peptide on the secondary response to SRBC was also determined by administering the same doses of peptide and human IL-1$\beta$ but only with the first inoculation.

Four days after the second dose the mice were killed and the number of PFC/spleen was determined as in Example 1, after combining the complement with a rabbit serum against mouse immunoglobulin at a final dilution of 1:200.

The results, given in Table 1 and FIG. 4, show an increase in the total PFC/spleen in the presence of peptide 163-171.TFA administered at various times, depending on the concentration used and at a maximum for a dose of 100 mg/kg.

TABLE I

Effect of different doses of peptide 163-171.TFA and human rIL-1$\beta$ on the secondary response to SRBC.

| Treatment[a] | Average of total anti-SRBC PFC-spleen (95% confidence limits) | p[b] |
|---|---|---|
| PBS | 21.528 (19.724-23.496) | — |
| Peptide 163-171 12 mg/kg | 38.019 (31.989-45.185) | ≦0.01 |
| Peptide 163-171 36 mg/kg | 40.457 (22.646-72.110) | ≦0.05 |
| Peptide 163-171 108 mg/kg | 44.987 (26.442-76.560) | ≦0.01 |
| PBS | 29.992 (18.365-51.050) | — |
| Peptide 163-171 100 mg/kg | 93.325 (69.023-126.182) | ≦0.01 |
| hu rIL-1$\beta$ 500 U/kg | 59.841 (45.604-78.343) | ≦0.01 |
| hu rIL-1$\beta$ 1000 U/kg | 77.624 (61.502-97.499) | ≦0.01 |
| hu rIL-1$\beta$ 2000 U/kg | 100.000 (84.139-118.850) | ≦0.01 |
| hu rIL-1$\beta$ 4000 U/kg | 42.364 (29.853-59.979) | n.s. |

[a]The mice intravenously inoculated with 1-2 × 10⁸ SRBC on day −10 and were given a similar dose on day 0 and simultaneously treated intraperitoneally with PBS (control) or with various doses of peptide 163-171.TFA or hu rIL-1$\beta$. The total number of anti-SRBC PFC was measured four days after the second inoculation of antigen.
[b]Statistical significance versus control.

EXAMPLE 5

Adjuvant effect of peptide 163-171.TFA on the thymo-independent antigen SIII

The procedure was the same as in Example 1: intraperitoneal inoculation with 0.5 ml of PBS containing 0.5 $\mu$g of polysaccharide of *Streptococcus pneumoniae* serotype 3 SIII (obtained from Phillips J. Baker NIAID, NIH, Bethesda) and, after two hours, with peptide 163-171.TFA and human interleukin 1-$\beta$.

After five days the mice were killed and the splenocytes were isolated from the spleen repeatedly washed and resuspended in MEM culture medium.

The adjuvant activity of peptide 163-171.TFA and of human IL-1-$\beta$ were then determined as in Example 1 by using 25 $\mu$l of a 10% suspension of SIII antigen conjugated with SRBC by chromium chloride in PBS (Baker P. J. et al. Appl. Microbiol. 17, 422 (1969)). By this method, 0.5 ml of sedimented SRBC were resuspended in 1 ml of saline solution containing 1 mg of SIII and 0.1 ml of a 0.1 solution of chromium chloride (Sigma Chemical Co, St. Louis) were then added to the first solution. The resulting mixture was kept under gentle agitation at ambient temperature (20°-25° C.) for 5 minutes.

The results, given in FIG. 4, show an increase in the number of PFC/spleen in the presence of peptide 163-171.TFA depending on the dose and at a maximum at a dose of 100 mg/kg.

EXAMPLE 6

Analysis of the immunostimulating activity of peptide 163-171.TFA intravenously inoculated, in comparison with the activity of peptide 163-171.HCl

A. Primary response to SRBC

The procedure was the same as in Example 1, i.e. intravenous inoculation of some mice with 0.2 ml of PBS containing peptide 163-171.TFA (from 1 pg/kg to 100 $\mu$g/kg) and other mice with 0.2 ml of PBS containing peptide 163-171.HCl (from 1 pg/kg to 100 $\mu$/kg).

The results, given in Table 2 hereinafter, show that the peptide 163-171.TFA preparation is more active when intravenously inoculated and that the peptide 163-171.HCl preparation is significantly more active than the 163-171.TFA preparation as regards the dose necessary for obtaining the optimum immunostimulating effect.

The maximum increase in the primary response to SRBC is obtained at doses of 10 pg-1 $\mu$g/kg of peptide 163-171.HCl and doses of 10-100 $\mu$g/kg of peptide 163-171.TFA.

TABLE 2

Comparison of the effects of peptide 163-171.TFA and 163-171.HCl on the primary response to SRBC

| Dose of peptide | PFC/spleen (% control) after | | | |
|---|---|---|---|---|
| | 163-171 TFA | | 163-171 HCl | |
| control | 42,364 (100.0%) | | | |
| 1 pg/kg | 41,400 | (97.7%)+ | 77,625 | (183.2%)** |
| 10 pg/kg | 41,400 | (97.7%)+ | 131,826 | (311.2%)** |
| 100 pg/kg | 44,610 | (105.3%)+ | 89,125 | (210.4%)** |
| 1 ng/kg | — | — | 90,573 | (213.8%)** |
| 10 ng/kg | 41,976 | (99.1%)+ | 80,456 | (189.9%)** |
| 100 ng/kg | — | — | 61,659 | (145.5%)** |
| 1 $\mu$g/kg | 77,090 | (182.0%)** | 60,256 | (142.2%)* |
| 10 $\mu$g/kg | 104,071 | (245.7%)** | — | |
| 100 $\mu$g/kg | 108,232 | (255.5%)** | 46,026 | (108.6%)+ |

+ n.s.
* p <0.05
** p <0.01

B) Secondary response to SRBC

The procedure was the same as in Example 4, the antigen being intravenously inoculated together with preparations of peptide 163-171.TFA and 163-171.HCl (from 100 pg/kg to 100 $\mu$g/kg in PBS).

The results in Table 3 hereinafter show that the maximum increase in secondary response to SRBC is obtained at a dose of 1 $\mu$g/kg of peptide 163-171.HCl, i.e. about 10,000 times less than the response observed int he case of peptide 163-171.TFA (100 $\mu$g/kg).

In addition, the optimum dose for intravenously inoculated trifluoroacetate peptide is lower than the dose (100 mg/kg) required when intraperitoneally introduced.

TABLE 3

Comparison of the effects of peptide 163-171.TFA and 163-171.HCl on the secondary response to SRBC.

| Dose peptide | Total PFC/spleen (% control) after | |
|---|---|---|
| | 163-171 TFA | 163-171 HCl |
| control | 20,091(100.0%) | |
| 100 pg/kg | 17,258 (85.9%)+ | 31,117 (154.9%)+ |
| 1 ng/kg | — — | — — |
| 10 ng/kg | 26,915 (134.0%)+ | 51,286 (255.3%)** |
| 100 ng/kg | — — | — — |
| 1 µg/kg | 31,405 (156.3%)* | 61,235 (304.8%)** |
| 10 µg/kg | — — | — — |
| 100 µg/kg | 61,659 (306.9%)** | 37,757 (187.9%)** |

+ n.s.
\* $p < 0.05$
\*\* $p < 0.01$

C) Primary response to SIII

The procedure was the same as in Example 5, i.e. intravenous inoculation of the preparations of the two peptides in concentrations from 1 pg to 100 pg/kg.

The results in Table 4 show significant increases in the response to antigen SIII at doses of 1-100 pg/kg of peptide 163-171.HCl.

At the same doses, the trifluoroacetate peptide is inactive.

TABLE 4

Comparison between the effects of peptide 163-171.TFA and 163-171.HCl on the primary response to SIII

| Dose of peptide | PFC/spleen (% control) after | |
|---|---|---|
| | 163-171 TFA | 163-171 HCl |
| control | 851 (100.0%) | |
| 1 pg/kg | 734 (86.3%)+ | 1,183 (139.0%)* |
| 10 pg/kg | 776 (91.2%)+ | 1,455 (171.0%)* |
| 100 pg/kg | 782 (91.9%)+ | 1,678 (197.2%)** |

+ n.s.
\* $p < 0.05$
\*\* $p < 0.01$

I claim:

1. A pharmaceutical composition capable in living organisms including man of potentiating the primary and secondary antibody response to antigens having low immunogenicity, comprising a solution of 1 pg to 100 mg/kg of the hydrochloride salt of the nonapeptide having the following formula:

Val-Gln-Gly-Glu-Glu-Ser-Asn-Asp-Lys-X where:
Val=L=Valine, Gln=L-Glutamine, Gly=Glycine, Glu=L-Glutamic acid, Ser=L-serine, Asn=L-Asparagine, Asp=L-aspartic acid, Lys=L-Lysine and X=OH in a pharmacologically acceptable solvent.

2. The pharmaceutical composition according to claim 1 wherein the antigens are thymodependent.

3. The pharmaceutical composition according to claim 1 wherein the antigens are thymoindependent.

4. The pharmaceutical composition according to claim 1 wherein the solvent is water or a saline phosphate buffer.

5. A method for potentiating in living organisms including man the primary and secondary antibody response to natural and/or synthetic thymodependent and thymoindependent antigens having low immunogenicity comprising administering the pharmaceutical composition according to claim 1.

6. A method of use of the pharmaceutical composition according to claim 1 as an adjuvant in a vaccine containing thymodependent and thymoindependent antigens having low immunogenicity.

7. A method for amplifying and prolonging the immune response to thymodependent and thymoindependent antigens having low immunogenicity comprising administering the pharmaceutical composition according to claim 1 to a living organism including man, together with or separately from the antigens.

8. A method according to claim 7 wherein the antigens are synthetic.

9. A method according to claim 7 wherein the antigens are natural.

10. A method according to claim 7 wherein the administration is intravenous, intramuscular or intraperitoneal.

11. A method as defined in claim 7 wherein the administration is intravenous.

* * * * *